US012564619B2

(12) United States Patent　　(10) Patent No.: US 12,564,619 B2

Sathe et al.　　(45) Date of Patent: *Mar. 3, 2026

(54) STABLE FORMULATIONS OF RECOMBINANT PROTEINS

(71) Applicant: Unichem Laboratories Ltd, Mumbai (IN)

(72) Inventors: Dhananjay Sathe, Maharashtra (IN); Bijay Padhi, Hyderabad Telengana (IN); Vivek Mishra, Madhya Pradesh (IN); Anupam Jain, Madhya Pradesh (IN)

(73) Assignee: Unichem Laboratories Ltd, Mumbai (IN)

( * ) Notice: Subject to any disclaimer, the term of this patent is extended or adjusted under 35 U.S.C. 154(b) by 682 days.

This patent is subject to a terminal disclaimer.

(21) Appl. No.: 17/623,748

(22) PCT Filed: Jul. 7, 2020

(86) PCT No.: PCT/IB2020/056361

§ 371 (c)(1),
(2) Date: Dec. 29, 2021

(87) PCT Pub. No.: WO2021/005500

PCT Pub. Date: Jan. 14, 2021

(65) Prior Publication Data

US 2022/0339241 A1　　Oct. 27, 2022

(30) Foreign Application Priority Data

Jul. 9, 2019　　(IN) .............................. 201921027358

(51) Int. Cl.

| | |
|---|---|
| *A61K 38/00* | (2006.01) |
| *A61K 9/19* | (2006.01) |
| *A61K 36/07* | (2006.01) |
| *A61K 38/16* | (2006.01) |
| *A61K 47/18* | (2017.01) |
| *A61K 47/22* | (2006.01) |
| *A61K 47/26* | (2006.01) |

(52) U.S. Cl.

CPC ................ *A61K 38/16* (2013.01); *A61K 9/19* (2013.01); *A61K 36/07* (2013.01); *A61K 47/183* (2013.01); *A61K 47/22* (2013.01); *A61K 47/26* (2013.01)

(58) Field of Classification Search

CPC .......... A61K 38/16; A61K 9/19; A61K 36/07; A61K 47/183; A61K 47/22; A61K 47/26

See application file for complete search history.

(56) References Cited

U.S. PATENT DOCUMENTS

| | | | | |
|---|---|---|---|---|
| 2014/0023664 A1* | 1/2014 | Lowman | .............. | G01N 33/574 |
| | | | | 435/69.6 |
| 2014/0155485 A1* | 6/2014 | Bannister | .............. | A61K 47/14 |
| | | | | 514/570 |
| 2018/0311294 A1* | 11/2018 | Peltier | .................... | A61K 36/67 |

FOREIGN PATENT DOCUMENTS

| | | | | |
|---|---|---|---|---|
| CN | 101918439 | * | 12/2010 | ......... C07K 14/4726 |
| CN | 101918439 A | * | 12/2010 | ......... C07K 14/4726 |
| WO | WO-2010095143 A2 | * | 8/2010 | ............. C07K 14/37 |
| WO | WO-2020104911 A1 | * | 5/2020 | ........... A61K 31/337 |

OTHER PUBLICATIONS

Yau et al (Molecules 2015 vol. 20, pp. 3791-3810 review the topic of âLectins with Potential for Anti-Cancer Therapyâ. (Year: 2015).*

Peppa et al "Molecular Cloning, Carbohydrate Specificity and the Crystal Structure of Two Sclerotium rolfsii Lectin Variants" (Molecules 2015, vol. 20: pp. 10848-10865). (Year: 2015).*

Saurabh et al., "Understanding the Stabilizing Effect of Histidine on mAb Aggregation: A Molecular Dynamics Study," Molecular Pharmaceutics, vol. 19, pp. 3288-3303 (Aug. 11, 2022).

* cited by examiner

*Primary Examiner* — Catherine S Hibbert

(74) *Attorney, Agent, or Firm* — BACON&THOMAS,PLLC

(57) ABSTRACT

The present invention relates to stable formulations of recombinant proteins. The invention specifically relates to the formulations of recombinant lectins derived from *Sclerotium rolfsii* lectin. The formulation comprises recombinant lectin derived from *Sclerotium rolfsii* lectin and a pharmaceutically acceptable excipient. The invention also relates to the stable liquid and/or lyophilized formulations comprising recombinant lectins derived from *Sclerotium rolfsii* lectin.

14 Claims, No Drawings

Specification includes a Sequence Listing.

STABLE FORMULATIONS OF RECOMBINANT PROTEINS

SEQUENCE LISTING INCORPORATION BY REFERENCE STATEMENT

A sequence listing ASCII text file is incorporated herein by reference. The sequence listing ASCII text file is named "PCT20 IN0529-seql-000001.txt," created Jul. 7, 2020. The size of the sequence listing ASCII text file is 5659 bytes.

FIELD OF INVENTION

The present invention relates to recombinant proteins derived from soil borne fungus and their therapeutically effective formulations. The invention specifically relates to the recombinant lectins derived from *Sclerotium rolfsii* lectin and their stable liquid and/or lyophilized formulations.

BACKGROUND OF INVENTION

Development of recombinant proteins was an important breakthrough in biomedical biotechnology. They are known as highly potent medicines that are safe from off-target side effects and are used for treating diseases such as diabetes, dwarfism, myocardial infarction, congestive heart failure, cerebral apoplexy, multiple sclerosis, neutropenia, thrombocytopenia, anaemia, hepatitis, rheumatoid arthritis, asthma, Crohn's disease, and cancer. Recombinant hormones, interferons, interleukins, growth factors and enzymes are some of the recombinant proteins approved by regulatory authorities and are available as medicines as of today.

Lectins are carbohydrate-binding proteins, macromolecules that are highly specific for sugar moieties of other molecules. Many lectins are used as biomarkers indicating early detection of malignant growth or as autophagy inducers while other lectins also show the ability to inhibit cancerous growth through apoptosis. Lectins are used as a drug delivery agent in cancer therapy because they bind specifically to the malignant tumours. Further since the lectins also modulate cancer associated pathways they have potential as cancer diagnostic and therapeutic agents. Currently, most commercially available lectins are from plants and other eukaryotes.

*Sclerotium rolfsii* lectin (SRL) is a lectin that has been isolated from the sclerotial bodies of the soil-borne phytopathogenic fungus *S. rolfsii*. SRL has specificity towards Thomsen-Friedenreich (TF) antigen and Tn antigen. TF antigen is a disaccharide (Galβ1→3GalNAc-α-Ser/Thr) that is over-expressed on the cell surface of different human cancer cells. Tn antigen is a monosaccharide (GalNAc-α-). Due to its specificity for TF and Tn antigen, SRL has been shown to bind to human colon cancer, ovarian cancer and leukemic cells.

WO 2010/095143 discloses recombinant lectin variants Rec-2 and Rec-3, which are derived from the native SRL sequence by the substitution of 3 and 5 amino acids respectively. Similarly WO 2014/203261 discloses a recombinant lectin variant derived from the native SRL sequence by the substitution of 12 amino acids.

Even though WO 2010/095143 and WO 2014/203261 demonstrate that the lectins derived from SRL are highly potent against several cancers such as human colon cancer, ovarian cancer and leukemic cells, the references remain silent about their therapeutic formulations for the effective treatment of cancers in human.

There are references wherein compositions comprising lectin (other than those derived from SRL) are disclosed. The references WO03010188, WO2003018617, WO03090774 and CN101485880 disclose compositions of mannose binding lectins comprising isotonicity agents, stabilizers, buffers and carriers.

JP2011126907 discloses a pharmaceutical composition that induces apoptosis in brain tumor cells, and comprises a lectin having binding specificity for the N-linked sugar chain A2G2F of glycoprotein. WO2014027958 and U.S. Pat. No. 9,981,007 are related to pharmaceutical composition comprising a recombinant Mistletoe lectin, which is a plant lectin, whereas RU2644332 relates to the composition of protein extracted from Mistletoe having an antitumor effect and stability for two and a half years.

Thus there are no reports on therapeutically effective formulations of fungal lectins for efficient treatment of cancers in human. Further lectin being macromolecule as compared to organic compounds (traditional active pharmaceutical ingredients), development of their formulations is extremely complex and challenging. Major challenges are stability of the lectin in the formulation and the preservation of the conformational integrity of at least a core sequence of the amino acids in the lectin. The stability is of concern due to highly degradative nature of such large proteins, which may result from chemical instability (e.g., any process which involves modification of the protein by bond formation or cleavage resulting in a new chemical entity) or physical instability (e.g., changes in the higher order structure of the protein). Chemical instability might result from deamidation, racemization, hydrolysis, oxidation, beta elimination or disulfide exchange and physical instability might be due to denaturation, aggregation, precipitation or adsorption. A marketable protein formulation must be safe to administer, remain physically, chemically, and biologically stable during the recommended shelf life.

There is need of an hour to develop stable and efficient formulation of fungal lectins that are effective for cancer treatment. Also it is necessary to develop a stable formulation while maintaining solubility and bioactivity of the lectin. Therefore it is an object of the invention to develop a stable formulation of lectin derived from fungus. Also it is an object to develop a pharmaceutically acceptable, therapeutically effective formulation of lectin. In certain embodiments, it is an object to provide a lectin formulation which is suitable for enteral or parenteral administration. It is a further object to provide a stable lyophilized lectin formulation which is easy to handle, store and deliver.

SUMMARY OF THE INVENTION

According to an aspect of the present invention there is provided a stable pharmaceutical composition comprising therapeutically effective amount of recombinant lectin protein derived from *Sclerotium rolfsii* lectin (SRL).

According to the specific aspect of the present invention, there is provided a stable pharmaceutical composition comprising therapeutically effective amount of recombinant lectin derived from SRL, wherein the recombinant lectin comprises or consists of an amino acid sequence selected from:
- a) SEQ ID NO 1,
- b) SEQ ID NO 2;
- c) SEQ ID NO 3; or
- d) an amino acid sequence having at least 60%, at least 70%, at least 80%, at least 90%, at least 95%, at least 97%, at least 98% or at least 99% homology with SEQ ID NO:1, 2 or 3.

*Sclerotium rolfsii* lectin or SRL is a protein having amino acid sequence of SEQ ID NO: 4. SEQ ID NOS. 1 to 3 are examples of amino acid sequences having at least 60% homology to SEQ ID NO. 4. In particular, SEQ ID NOS. 1, 2 and 3 have a homology of 97.9%, 96.5% and 91.5% to SEQ ID NO. 4, respectively (as determined using EMBOSS Needle).

According to any one of the preceding aspects, the recombinant lectin is a modified lectin protein (that is a recombinant lectin protein having at least one amino acid modification in a carbohydrate binding site) as defined in WO2020/044296 which is incorporated herein by reference, in particular with regard to the definition of the lectin.

In some embodiments the stable pharmaceutical composition of the present invention comprises therapeutically effective amount of recombinant lectin derived from *Sclerotium* lectin and pharmaceutically acceptable excipients.

In another embodiment the pharmaceutically acceptable excipient comprises one or more pharmaceutically acceptable stabilizer.

According to any one of the preceding aspects, the pharmaceutically acceptable stabilizer comprises at least one of:

(a) one or more amino acid or its pharmaceutically acceptable salt;

(b) one or more surfactant;

(c) one or more carbohydrate or sugar; or (d) mixture of two or more of a) to c).

In an embodiment, the pharmaceutically acceptable stabilizer comprises:

(a) one or more amino acid or its pharmaceutically acceptable salt;

(b) one or more surfactant; and/or (c) one or more carbohydrate, wherein the ratio of recombinant lectin to (i) amino acid or its pharmaceutically acceptable salt is in the range from about 1:0.1 to about 1:10;

(ii) surfactant is in the range of about 1:0.0002 to about 1:10; and (iii) carbohydrate is in the range from about 1:0.1 to about 1:150.

According to any one of the preceding aspects, the stable pharmaceutical composition of the present invention is administered locally, enterally or parenterally.

Further according to any one of the preceding aspect of the present invention the stable pharmaceutical composition is used for the treatment or prevention of cancer.

According to yet another aspect of the present invention there is provided a process to prepare stable pharmaceutical composition comprising therapeutically effective amount of recombinant lectin derived from *Sclerotium rolfsii* lectin.

According to another aspect of the present invention there is provided a formulation stabilizing component comprising at least one of:

(a) one or more amino acid or its pharmaceutically acceptable salt;

(b) one or more surfactant;

(c) one or more carbohydrate or sugar; or (d) mixture of two or more of a) to c).

According to the specific aspect of the present invention there is provided a stable pharmaceutical composition comprising:

(a) about 0.0001% (w/v) to about 10% (w/v) of recombinant lectin protein derived from *Sclerotium rolfsii* lectin;

(b) about 0.01% (w/v) to about 10% (w/v) of one or more amino acid or its pharmaceutically acceptable salt;

(c) about 0.0001% (w/v) to about 1% (w/v) of one or more surfactant; or (d) about 0.1% (w/v) to about 15% (w/v) of one or more carbohydrate or sugar.

The percentage used herein refers to the amount (weight) of the component in the final formulation in volume ready for administration. The percentage is determined by the methods known in the prior art.

BRIEF DESCRIPTION OF THE ACCOMPANYING SEQUENCES

SEQ ID NO. I: represents a variant of the *S. rolfsii* lectin amino acid sequence (reported as Rec-2 in WO 2010/095143).

SEQ. ID NO. 2: represents a variant of the *S. rolfsii* lectin amino acid sequence (reported as Rec-3 in WO 2010/095143).

SEQ ID NO. 3: represents a variant of the *S. rolfsii* lectin amino acid sequence (reported in WO 2014/203261).

SEQ ID NO. 4: represents the native *S. rolfsii* lectin amino acid sequence.

DETAILED DESCRIPTION OF INVENTION

Definitions

The term "lectin" as used herein refers to a carbohydrate-binding protein, wherein the term "protein" as used herein refers to a polymer of amino acid residues.

The term "recombinant" product, as used herein, refers to a genetically engineered product. It will be appreciated that genetic engineering is the non-natural manipulation of genes. Thus a recombinant product is a product which exists or is synthesized in a non-natural environment such as a host cell in which the product is not present in nature.

The term "recombinant protein", "recombinant lectin", recombinant lectin protein or "recombinant polypeptide" as used herein refers to a protein molecule which is expressed using a recombinant DNA. molecule. The recombinant protein according to present invention is the lectin derived from *Sclerotium rolfsii* lectin (SRL). SRL is a lectin that has been isolated from the sclerotial bodies of the soil-borne phytopathogenic fungus *S. rolfsii*. Protein having amino acid sequence of SEQ ID No 1 is an example of recombinant lectin.

The term "recombinant protein" is intended here to cover any pharmaceutically acceptable salt, solvate, hydrate, prodrug, or any other compound which, upon administration to the patient is capable of providing (directly or indirectly) the compound as described herein. The preparation of salts, solvates, hydrates, and prodrugs can be carried out by methods known in the art.

The terms 'formulation', 'composition', 'pharmaceutical formulation' and 'pharmaceutical composition' are used interchangeably and refer to preparations which are in such a form as to permit the biological activity of the active ingredients to be effective, and, therefore may be administered to a subject for therapeutic use, wherein the subject is preferably human. 'Active ingredients' as used herein refers to the recombinant lectin or recombinant protein having desired biological or therapeutic activity to free the subject from the disease or symptoms of disease or slow or delay the progression of the disease. The formulation of the present invention are prepared as liquid formulation or solid formulation. A Liquid formulation is in the form of solutions, emulsions or suspensions suitable for oral administration or injection. It will be appreciated by the person skilled in the art that the liquid formulation is in the medium such as water for injection (WFI) as a liquid vehicle. The solid formulation is either prepared by mixing solid ingredients or by evaporating the solvent medium. The solid formulations can also be prepared by lyophilisation of the liquid formulation, wherein in the process of lyophilisation, material to be dried is first frozen and then the ice or frozen solvent is removed by sublimation under vacuum. For stability reasons excipients may be added in the preparation before it is lyophilised. During lyophilisation it may be necessary to identify and employ appropriate shelf temperatures, product temperatures, vacuum levels, freezing, primary• drying parameters, and secondary drying parameters, which is in the ambit of the knowledge of the person skilled in the art. The solid formulation may also be known as lyophilized formulation.

The term 'excipient' as used herein refers to inactive or usually inert substances that are added to the formulation which do not affect the therapeutic action of the active ingredient, but serves as the vehicle or medium for the active ingredient. It may be used to provide a desired consistency, to improve stability, and/or to adjust osmolality of the composition. For the purpose of this invention excipients may be selected from the substances that are known to the skilled person for use in the protein formulations. Examples of such excipients are buffers, protein stabilizing agents, polymers, solubilizers, cryoprotectants, lyoprotectants, bulking agent/s diluents or mixture thereof.

The term "Cryoprotectant" as used herein refers to compounds which prevent cells or tissues or the active ingredient in the formulation from damage due to freezing or during the process of freezing.

The term "Lyoprotectant" as used herein refers to compounds which prevent cells or tissues or the active ingredient in the formulation from damages during the drying stages.

The cryoprotectant and lyoprotectant can also be used as the bulking agents. Bulking agent strengthens the structure of the resulting lyophilized cake and are as understood by the person skilled in the art.

The term 'therapeutically effective amount' as used herein is an amount sufficient to effect desired clinical results (i.e., achieve therapeutic efficacy). A therapeutically effective amount can be administered in one or more administrations. For purpose of this invention, a therapeutically effective amount of a recombinant protein is an amount that is sufficient to palliate, ameliorate, stabilize, reverse, prevent, slow or delay the progression of the disease state.

The terms "homology" or "homologous" as used herein refer to two or more referenced entities that share at least partial identity over a given region or portion. Areas, regions or domains of homology or identity refer to a portion of two or more referenced entities that share homology or are the same. Thus, where two sequences are identical over one or more sequence regions they share identity in these regions. Substantial homology refers to a molecule that is structurally or functionally conserved such that it has or is predicted to have at least partial structure or function of one or more of the structures or functions (e.g., a biological function or activity) of the reference molecule, or a relevant/corresponding region or portion of the reference molecule to which it shares homology.

Room temperature is temperature in the range from 22° C. to 28° C.

The terms 'stable composition' and 'stable formulation' as used herein have the same meaning and refer to the composition of protein in which the protein therein essentially retains its physical and chemical stability and integrity and its therapeutic efficacy upon storage. The protein in the composition does not undergo any modification by bond formation or cleavage or there is no modification in the basic structure of the protein. For example, a "stable" formulation may be one wherein less than about 10% and preferably less than about 5% of the protein is present as an aggregate in the formulation. Additionally, a stable formulation can also offer protection against aggregation or precipitation of the proteins dissolved therein. The stability of the protein formulation may also be measured using a biological activity assay (bioassay). The stable composition is expected not to exhibit considerable variations in the value of assay during the shelf life as compared to the freshly prepared composition.

For example, in the present invention the bioassay was observed by testing the cytotoxicity of the formulation against ovarian cancer cell line (PA-1 Cell line). The standard cytotoxicity of SEQ ID NO 1 in buffer, against PA-1. Cell line is between 31.58% and 58.05%. The composition of SEQ ID NO 1 is expected to exhibit similar effect on PA-1 cell line. If the effect of the composition at zero month and after 6 months on said cell line is same (between 31.58% and 58.05%) then the composition is said to stable for 6 months.

The stability of the composition may also be tested using several other parameters. For example the composition is said to be stable for 6 months if it does not change its appearance during 6 months when observed with naked eyes. Or the composition is said to be stable composition if the impurities formed during stability period, for example after 1 month to up to 6 months of preparation of the formulation, are in the acceptable limits. The impurities may include high molecular weight impurities or other unknown impurities.

Further the composition may be said to be stable if its 'assay' is same or within acceptable limits during the stability period. The term "Assay" used herein refers to an analytical procedure for determination of purity or strength of the active substance. It is the analysis of percentage of active ingredient present in the composition. The assay to analyse protein may be selected from the methods known in the art such as chromatographic methods or chemical analysis or titrations. The percentage of protein in the formulation should be same or variable within limits when analysed after stability period as that was on the day of preparation.

The term "Stability period" used herein refers to a time period during which the formulation and the active components in the formulation retain all its properties such as identity, strength, quality, purity and activity. The stability period is calculated from the date of preparation or manufacturing of the formulation and may vary from days, to weeks, to months to years. For example a formulation may exhibit stability for couple of days from preparation or may remain stable for 3 years from the date of preparation.

'Formulation stabilizing component' refers to a substance that reduces or prevents degradation of protein in aqueous solution, during freezing step, or during freeze-drying. 'Formulation stabilizing component' maintains the protein conformation under different conditions. Variety of formulation components such as buffering agents, surface-active agents, amino acid stabilizers, carbohydrate stabilizers and tonicity adjustment agents are employed individually or in combination so as to stabilize the protein and therefore the protein formulation.

The term "Amino acids", when referred to as a component or excipient of the formulation is a simple organic compound containing both a carboxyl (—COOH) and an amino (NH$_2$) group. For the purpose of the present invention amino acids are employed as protein stabilizers individually or as a mixture thereof or in combination with the other stabilizing components.

The term 'w/v' as used herein refer to the weight percentage of an excipient in the composition and is measured or calculated as understood by the skilled person.

The terms "cancer", "tumor" and "tumour", may be used interchangeably in the present application, as would be understood by the person skilled in the art. Cancers or tumours result from abnormal cell growth. They form when the normal cells grow out of control and crowd out. Formation of tumours often affects the normal functioning of the tissue, organ or organism.

Cancer can start any place in the body and can also spread to other parts of the body. The spread of cancer cells is referred to as metastasis. Thus the term "cancer" encompasses both primary and metastatic cancers. As used herein, the term "cancer" includes, but is not limited to, solid tumors.

It will be understood that the term "treatment" may comprise substantially curing the cancer, preventing or slowing the progression of, or reducing the severity of, the disease, preventing or reducing metastases, inhibiting tumour growth, reducing tumour mass or eliminating tumours, and/or ameliorating (either temporarily or permanently) symptoms associated with the disease. It will be appreciated that symptoms will vary• depending on the type of cancer, but may include pain, reduction or loss of function, nausea and/or sickness, fever, tumour formation, immunosuppression, and/or tiredness. The term "treatment" includes a prophylactic or therapeutic or preventive measure.

The term "Reconstitution time" is the time required to completely dissolve a solid formulation such as lyophilized formulation in a liquid, to a clarified solution, free of particles. As appreciated by the skilled person, the short period of time required for reconstitution of the lyophilized formulation is a contributing factor in determination of stability of the formulation. The quantity of liquid, which usually is the water for injection, added would depend on the final concentration of the protein required in the formulation before administration of the formulation to the subject.

According to the first specific aspect of the present invention, there is provided a stable pharmaceutical composition comprising therapeutically effective amount of recombinant lectin protein derived from *Sclerotium rolfsii* lectin.

According to the another aspect of the present invention, there is provided a stable pharmaceutical composition comprising therapeutically effective amount of recombinant lectin derived from SRL, wherein the recombinant lectin comprises or consists of an amino acid sequence selected from:

(a) SEQ ID NO 1;
(b) SEQ ID NO 2;
(c) SEQ ID NO 3; or
(d) an amino acid sequence having at least 60%, at least 70%, at least 80%, at least 90%, at least 95%, at least 97%, at least 98% or at least 99% homology with SEQ ID NO:1, 2 or 3.

In one embodiment, the percentage "homology" between two sequences is determined using the BLASTP algorithm with default parameters (Altschul et al. Nucleic Acids Res. 1997 Sep. 1; 25 (17): 3389-402). In particular, the BLAST algorithm can be accessed on the internet using the URL: https://blast.ncbi.nlm.nih.gov/Blast.cgi. In an alternative embodiment, for global sequence alignments, percentage identity homology between two sequences is determined using the EMBOSS Needle algorithm using default parameters. In particular, the EMBOSS Needle algorithm can be accessed on the internet using the URL: [www.]ebi.ac.uk/Tools/psa/emboss_needle/.

*Sclerotium rolfsii* lectin or SRL is a protein having amino acid sequence of SEQ ID NO: 4. SEQ ID NOS. I to 3 are examples of amino acid sequences having at least 60% homology to SEQ ID NO. 4. In particular, SEQ ID NOS. 1, 2 and 3 have a homology of 97.9%, 96.5% and 91.5% to SEQ ID NO. 4 respectively (as determined using EMBOSS Needle).

SEQ ID NO: I. represents a variant of the SRL amino acid sequence (reported as Rec-2 in WO 2010/09.51.43).

SEQ ID NO: 2: represents a variant of the SRL amino acid sequence (reported as Rec-3 in WO 2010/095143).

SEQ ID NO: 3: represents a variant of the SRL amino acid sequence (reported in WO 2014/203261).

SEQ II) NO: 4: represents the native *S. rolfsii* lectin amino acid sequence.

According to any one of the preceding aspects, the recombinant lectin is a modified lectin protein (i.e. a recombinant lectin protein having at least one amino acid modification in a carbohydrate binding site) as defined in WO2020/044296 which is incorporated herein by reference, in particular with regard to the definition of the lectin. In a specific aspect, the recombinant lectin comprises at least one amino acid modification in a carbohydrate binding site of SEQ ID NO. 4 or an amino acid sequence having at least 60% homology to SEQ ID NO. 4.

In another specific aspect, the carbohydrate binding site is a primary and/or secondary carbohydrate binding site.

In another specific aspect, the primary• carbohydrate binding site comprises a position selected from 1 or more of 27, 28, 47, 48, 70, 71.72 & 105 in SEQ ID NO. 1 or in an amino acid sequence having at least 60% homology to SEQ ID NO. 4.

In another specific aspect, the position of the amino acid modification is selected from one or more of:

(a) 27 and/or 28;
(b) 47 and/or 48;
(c) 70, 71, and/or 72; and/or
(d) 105

In another specific aspect, the secondary' carbohydrate binding site comprises a position selected from one or more of 77, 78, 80, 101, 112, and 114 in SEQ ID NO. 4 or in an amino acid sequence having at least 60% homology to SEQ ID NO. 4.

In another specific aspect, the position of the amino acid modification is selected from one or more of:

(a) 77, 78, and/or 80;
(b) 101; and/or
(c) 112, and/or 114.

In another specific aspect, the amino acid modification is an amino acid substitution such that a substituting amino acid replaces an. original amino acid.

In another specific aspect, the amino acid substitution in the primary• carbohydrate binding site is selected from one or more of:

(a) at position 27: a conservative, favourable or unfavourable amino acid, wherein the conservative amino acid is non-polar or acidic; favourable is polar or basic and unfavourable amino acid is non-polar;
(b) at position 28: a conservative, favourable, neutral or unfavourable amino acid, wherein the conservative amino acid is non-polar; favourable is polar, neutral is acidic or basic and unfavourable amino acid is polar;

(c) at position 47: an unfavourable amino acid, which is basic or non-polar;

(d) at position 48: an unfavourable amino acid, which is non-polar;

(e) at position 70: an unfavourable amino acid, which is non-polar;

(f) at position 71: an unfavourable amino acid, which is non-polar;

(g) at position 72: an unfavourable amino acid, which is non-polar; and/or (h) at position 105: a conservative, favourable, neutral or unfavourable amino acid, wherein the conservative amino acid is basic or non-polar; favourable is polar, neutral is acidic, basic or polar and/or unfavourable amino acid is polar, non-polar or acidic.

In another specific aspect, the amino acid substitution in the secondary carbohydrate binding site is selected from one or more of:

(a) at position 77: an unfavourable amino acid which is non-polar;

(b) at position 78: an unfavourable amino acid which is non-polar;

(c) at position 80: an unfavourable amino acid which is non-polar;

(d) at position 101: a favourable, an unfavourable or a neutral amino acid, wherein the favourable amino acid is polar or basic, the unfavourable amino acid is non-polar and the neutral amino acid is non-polar or acidic;

(e) at position 112: an unfavourable amino acid which is non-polar;

(f) at position 114: an unfavourable amino acid which is polar.

In another specific aspect, the modified lectin protein comprises at least one amino acid modification in the N-terminus of SEQ ID NO. 4 or in an amino acid sequence having at least 60% homology to SEQ ID NO. 4, wherein the N-terminus comprises a position selected from: I and/or 2 in SEQ ID NO. 4 or a corresponding position in the sequence having at least 60%, 70%, 80%, 90%, 95%, 97% or 99% homology thereto.

In another specific aspect, the amino acid modification is an amino acid substitution at position I and wherein a substituting amino acid is not threonine or valine.

In another specific aspect, the substituting amino acid is selected from: alanine, glycine, proline or serine.

In another specific aspect, the amino acid modification is an amino acid substitution at position 2 and wherein a substituting amino acid is tryptophan.

In another specific aspect, cleavage of an initiator methionine is increased or decreased as compared with a control.

In another specific aspect, the amino acid modification at position 76 is an amino acid substitution with a non-polar amino acid.

In another specific aspect, the non-polar amino acid is selected from: glycine, valine or leucine.

In another specific aspect, the amino acid modification at position 44 or 89 is an amino acid substitution with a non-polar amino acid.

In another specific aspect, the non-polar amino acid is selected from: leucine, isoleucine or valine.

In another specific aspect, the modified lectin protein is soluble, partially soluble or insoluble and/or has cytotoxicity.

In another specific aspect, the modified lectin protein has a cytotoxicity that is at least 10%, 20%, 30%, 40%, 50%, 60%, 70%, 80%, or 90% of a control.

In another specific aspect, the modified lectin protein has a percentage cytotoxicity that is less than 10% of a control, or is absent of cytotoxicity.

In another specific aspect, the modified lectin protein has a percentage cytotoxicity that is at least a 10%, 20%, 30%, 40%, 50%, 60%, 70%, 80%, 90%, or 100% increase compared with that of a control.

In another specific aspect, the modified lectin protein is equal to or less than 500, 400, 300, 250, 200, or 150 amino acids in length.

The recombinant proteins as described above can be obtained by processes described in WO2020/044296, WO2010/095143 and WO2014/203261. The recombinant proteins of the present invention, which in one embodiment, are purified by conventional techniques, typically conventional chromatographic methods.

According to another main aspect, the present invention provides a stable pharmaceutical composition comprising therapeutically effective amount of recombinant lectin derived from *Sclerotium roifii* lectin and pharmaceutically acceptable excipients.

The pharmaceutically acceptable excipients may be a buffer, a stabilizer, a polymers, a solubilizer, cryoprotectants, lyoprotectants, bulking agents, diluents emulsifiers and preservatives. The buffer for example may be selected from sodium phosphate, sodium monohydrogen phosphate dehydrate, sodium dihydrogen phosphate dehydrate, sodium citrate, sodium acetate, TM-sodium chloride, phosphate buffer such as dibasic potassium phosphate, monobasic potassium phosphate or histidine. The concentration of the buffer may range from 1 mM to 300 mM. As understood by the skilled person, in the buffer TRIS-sodium chloride buffer system the concentration of TRIS (trisaminomethane) is I mM-200 mM and the concentration of sodium chloride (NaCl) is 1 mM-300 mM. It will be appreciated that buffer is used to maintain pH of the formulation. The pH may be regulated between 5 and 9. In particular the pH of the formulation is in the range from 7 to 9.

According to an aspect of the invention the stabilizer may be selected from surfactants, detergents, amino acids, pharmaceutically acceptable salt of amino acid, carbohydrates or sugar stabilizers, amines, polyols or combination thereof.

According to this embodiment the non-limiting examples of surfactants are TWEEN® 20 (Polysorbate 20), TWEEN® 40 (Polysorbate 40), TWEEN® 60 (Polysorbate 60), TWEEN® 80 (Polysorbate 80), Sorbitan monolaurate, Sorbitan monopalmitate, Sorbitan monostearate, Sorbitan tristearate, Sorbitan monooleate, TRITON™ X-100, PLURONIC® F-68, PLURONIC® F-88, PLURONIC® F-127 (poloxamers), Sorbitan Monolaurate, Sorbitan Monosterate, Sorbitan tristearate, Poloxamer 188 and BRIJ™ 35 (polyoxyethylene alkyl ether) or combination thereof.

In some embodiment, the surfactant may be in the range from 0.001 mg/ml to 10 mg/ml or from 0.0001% (w/v) to 1.0% (w/v).

In some embodiment, a stable composition comprises recombinant lectin derived from *Sclerotium rolfsii* lectin and one or more surfactant, wherein the ratio of protein to surfactant is in the range from 1:0.0002 to 1:10.

Further according to an embodiment the amino acid may be selected from glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, arginine or combination thereof. The amino acid may be L-amino acid or D-amino acid, preferably L-amino acid. The amino acid may be used as such or as its salt. The salt may be an alkali salt or an alkaline earth metal salts, ammonium salts, organic amine salts such as triethylamine salt or triethanolamine salt, arginine salt such as basic amino acid salts or acid salts for example, hydrochloride, hydrobromide, sulfate, nitrate, phosphate, mineral acid salts citric acid salt, oxalate, tartrate or any other salt of amino acid as known to the skilled person. In one embodiment, the amino acid is selected from L-Histidine, L-Arginine, Glutamic acid or Methionine. In another embodiment, the amino acid is a hydrochloride salt of amino acid selected from L-Histidine, L-Areinine, Glutamic acid or Methionine. In a preferred embodiment the amino acid is selected from hydrochloride salt of L-Histidine or L-Arginine.

In some embodiments the concentration of amino acid or its pharmaceutically acceptable salt is in the range of 0.01% (w/v) to 10% (w/v) or from 0.1 mg/ml to 100 mg/ml.

In another embodiment a stable composition comprises recombinant lectin derived from *Sclerotium rolfsii* lectin and one or more amino acid or its pharmaceutically acceptable salt. The ratio of protein to amino acid or its pharmaceutically acceptable salt is in the range from 1:0.1 to 1:10.

According to yet another embodiment the carbohydrate or sugar stabilizers may be selected from the non-limiting examples of sucrose, trehalose, sorbitol, glycerol, mannitol, lactose, xylitol, arabitol, erythritol, lactitol, maltitol, Glucose, Raffinose, Maltose, dextran, inositol or combinations thereof. In some embodiments, the carbohydrate is sucrose or mannitol. In another embodiment the concentration of carbohydrate is in the range from 0.1% (w/v) to 15% (N' Iv) or from 1.0 mg/ml to 150.0 mg/ml.

In yet another embodiment, a stable composition comprises recombinant lectin derived from *Sclerotium rolfsii* lectin and one or more carbohydrate or sugar stabilizers, wherein the ratio of protein to carbohydrate is in the range from 1:0.1 to 1:150.

According to the aspect of the invention the stabilizer may further be selected from Amines like basic proteins such as protamine or pharmaceutically acceptable salt of protamine or natural or synthetic polymers bearing amine-residues such as polylysine. Protamine may be obtained or derived from, for example, human or fish. The stabilizer may also be selected from polyols such as PEG 400 to PEG 20,000, glycerol or xylitol.

In a particularly preferred embodiment, the stabilizer is a combination of one or more of surfactants, amino acids, pharmaceutically acceptable salt of amino acid and/or carbohydrates. For example the stabilizer may be a combination of surfactant and amino acid or may be the combination of amino acid or its salt and carbohydrate. U.S. Pat. No. 9,981,007 discloses a composition comprising recombinant mistletoe lectins for treating metastatic tumours, wherein according to the examples the composition comprises combination of polysorbate and glutamic acid or polysorbate and trehalose as stabilizer. It will be appreciated that, multiple stabilizers are used simultaneously in protein compositions in expectation of addressing different stability issues via different mechanisms and/or possible synergistic effects. However just use of multiple stabilizers does not always yield a stable protein formulation. For example in the present invention the formulation comprising L-T-listidine and varying amount of polysorbate 80 did not give a stable formulation. The visual inspection showed white precipitation after I month of storage at 25° C.

According to an aspect of the invention the excipients in composition may include polymer such as polyethylene glycols (PEGs), dextran, hydroxyl ethyl starch (HETA) or PEG-4000 or combination thereof; and a protein such as human serum albumin or Gelatin or combination thereof.

The compositions of the present invention may further optionally comprise preservatives such as benzyl alcohol, m-cresol, methyl paraben, phenol or combination thereof; tonicity modifier such as sodium chloride, dextrose, potassium chloride, calcium chloride, sucrose or combination thereof; a chelating agent such as Ethylene diamine tetra acetic acid; an antioxidant such as ascorbic acid, and/or a cryoprotectant such as mannitol, Ethylene glycol, Glycerol, sucrose, trehalose, and/or dextrose.

It will be appreciated that the examples of the excipients as mentioned herein are for the clarity and understanding of the invention and do not limit the invention in any manner. Further it will be also appreciated by the skilled person that the different excipients play different roles in the formulation. For examples polysorbate may be used in the formulation as a stabilizer or as a solubilizer or as an emulsifier. The formulations of the present invention comprise excipients exhibiting different functions and may not be restricted to the functions specified herein.

In some embodiments, the concentration of recombinant lectin in the composition is in the range from 0.001 mg/ml to 100 mg/mL In some embodiments, the concentration is at least 0.25 mg/ml, 0.5 mg/ml; at least 1 mg/ml, at least 1.5 mg/mL at least 2 mg/ml, at least 2.5 mg/ml, at least 3 mg/mi, at least 3.5 mg/ml, at least 4 mg/ml, at least 4.5 mg/ml, at least 5 mg/ml, at least 5.5 mg/ml, at least 6 mg/ml, at least 6.5 mg/ml, at least 7 mg/ml, at least 7.5 mg/ml, at least 8 mg/ml, at least 8.5 mg/ml, at least 9 mg/ml, at least 9.5 mg/ml, at least 10 mg/ml or, at least 20 mg/ml, at least 30 mg/ml, at least 40 mg/ml, at least 50 mg/ml.

In some embodiment, the concentration of recombinant lectin in the composition is in the range from 0.0001% (w/v) to 10% (w/v).

According to another main aspect of the present invention there provided a formulation stabilizing component comprising at least one of:

a) one or more amino acid or its pharmaceutically acceptable salt;

b) one or more surfactant;

c) one or more carbohydrate or sugar; or d) mixture of two or more of a) to c).

According to the aspect of the present invention the "formulation stabilizing component" is preferably used in the protein formulation.

In a specific embodiment the protein formulation is the formulation comprising recombinant lectin derived from *Sclerotium* lectin.

According to the very specific aspect, the stable pharmaceutical composition of the present invention comprises;

a) about 0.0001% (w/v) to about 10% (w/v) of recombinant lectin protein derived from *Sclerotium rolfsii* lectin;

b) about 0.01% (w/v) to about 10% (w/v) of one or more amino acid or its pharmaceutically acceptable salt;

c) about 0.0001% (w/v) to about 1% (w/v) of one or more surfactant; or d) d) about 0.1% (w/v) to about 15% (w/v) of one or more carbohydrate or sugar.

The composition of the present invention may be formulated as an aqueous liquid or solid. In some embodiment the composition may be liquid, suspension, powder, sterile powder or lyophilized for solution formulation. Lyophilized formulation may be reconstituted with Water for Injection (WFI) and/or any suitable pharmaceutically acceptable diluent or mixture thereof to get required concentration as known by the skilled person. The composition is suitable for single dose or multiple doses. A person skilled in the art knows that the type of dosing is dependent on various factors, such as the body height and weight, the body surface area, age, gender, or the general health of the patient, and on the preparation to be administered in particular, the duration and type of administration, and on other medications that may be administered in parallel.

The lectin may be provided in a pharmaceutically acceptable form, such as a liquid (e.g in an aqueous solution or suspension, or as an oil based solution or suspension), a solid (e.g a capsule or tablet), a lyophilized powder, a spray, cream, lotion or gel, vesicular drug delivery systems such as, but not limited to, bilosomes, liposomes, niosomes, transferosome, ethosomes, sphingosomes, pharmacosomes, multilamellar vesicles, microsphere and the like.

As used herein, an "aqueous solution" is a solution which is produced by dissolving a solid or lyophilized agent, such as a recombinant lectin having the amino acid sequence of SEQ ID NO. 1, in water or in a buffer containing water. An aqueous solution is also formed when an agent, such as a recombinant lectin having the amino acid sequence of SEQ ID NO.1, is in liquid form and is mixed with water or a buffer containing water.

The compositions of the present inventions may be administered to an individual in a suitable dosage. The administration can take place locally, enterally, or parenterally, for example, intravenously, intraperitoneally, subcutaneously, intramuscularly, locally, intranasally, intrabronchially or intradermally, or via a catheter at a point in an artery. In particular embodiment the compositions of present inventions may be administered parenterally.

In an embodiment, the liquid formulation of the present invention is stable at refrigerated temperature (2° C.-8° C.) for at least 2 years, or at least 1 year. In another embodiment, the liquid formulation is stable at room temperature for at least six months or at least three months or at least two months or at least one month.

In some embodiments, the lyophilized formulation of the present invention is stable at refrigerated temperature (2° C.-8° C.) for at least 2 years, or at least 1 year. In another embodiment, lyophilized formulation is also stable at room temperature for at least six months or at least five months or at least four months or at least 3 months. The lyophilized formulation is also stable at advanced temperature such as between 30° C. and 40° C. for at least four months or at least three months or at least two months or at least one month at least 15 days or at least 7 days.

According to another main aspect the composition of the present invention is used for the treatment or prevention of Cancer.

The term "cancer" includes diseases of the skin, tissues, organs, bone, cartilage. Examples of cancers that may be treated by the methods and compositions of the present invention include, but are not limited to, cancer of the bile duct, bladder, bone, brain, breast, cervix, colon, oesophagus, gastrointestine (including the ileum, colon, rectum and/or anus), head, kidney, liver, lung, nasopharynx, neck, ovary, pancreas, prostate, skin, stomach, testis, tongue, thyroid, urachus, vagina & uterus.

The cancer may be benign or malignant, and in any stage of malignancy.

The cancer may be a cancer of the epithelial tissues, non-epithelial tissues, the cells that make up the skin or the tissue lining the organs, cells of the immune system, connective tissue, or cells of the spinal cord or brain.

In some embodiments, the cancer is a solid tumour.

The cancer may be a carcinoma. In some embodiments, the cancer is adenocarcinoma. The adenocarcinoma may be oesophageal, pancreatic, prostate, cervical, breast, colon or colorectal, lung, bile duct, vaginal, urachus or stomach adenocarcinoma.

In some embodiments, the cancer is squamous cell carcinoma. The squamous cell carcinoma may be skin, oral, lung, thyroid, oesophagus, vaginal, cervical, ovarian, head and/or neck, prostate or bladder squamous cell carcinoma.

In some specific embodiment the cancer may be brain tumor/cancer, which might include Glioblastoma, meningioma, astrocytoma, glioma and neuroblastoma.

According to another embodiment the present invention provides a pharmaceutically stable composition of lectin for use in the treatment or prevention of Cancer in a subject in need thereof The subject may be a mammalian subject. For convenience, the mammal undergoing such 'treatment' can be referred to as a "subject". In some embodiments, the subject is human. In particular, the subject may be a human subject suffering from or seeking prevention or treatment from cancer. It will be appreciated by the skilled person that the subject may also be referred to as an 'individual'.

According to yet another main aspect of the present invention, there is provided a process to prepare stable composition, wherein the process comprises combining buffer solution of recombinant lectin with the buffer solution of one or more of the stabilizers. The process can be carried out at suitable conditions, according to the knowledge of the skilled person. For example the temperature during the process may be between 0° C. and 35° C., between 5° C. and 30° C., between 10° C. and 25° C. or between 20° C. and 25° C.

The stable composition may be liquid or lyophilized formulation. In a specific embodiment the process may comprise;

a) preparation of stock solution of recombinant lectin in buffer;

b) preparation of solution of single component of stabilizer;

c) addition of required quantity of solution a) to the required quantity of solution b);

d) optional dilution of mixture of step c) with required quantity of WFI;

e) optional addition of one or more stabilizers separately to the solution of step c) or step d);

f) addition of other excipients to the solution of step e);

g) making up of batch size using water for injection (WFD to obtain liquid formulation;

h) optionally lyophilisation of liquid formulation obtained in step g) to obtain lyophilized formulation.

As per the need and the understanding of the skilled person the steps in the process discussed above may be interchanged.

The pH of the formulation is maintained between 5 and 9, particularly between 7 and 9 using 0.05 N hydrochloric acid HCl). The composition is formulated at temperature between 0° C. and 35° C. Preferably at room temperature. The final liquid formulation may be aseptically filtered through a suitable filter such as 0.22 micron Polyvinylidene fluoride or Polyvinylidene difluoride (PVDF) or Polyethersulfone (PES) or any other such filter known to the skilled person.

EXAMPLES

The invention will be fully understood by reference to the following examples. They demonstrate the best mode of performing the invention and do not restrict the scope of the invention in any manner.

Example 1: Process to Prepare Aqueous/Liquid Formulations a) Stock solution of polysorbate 80 (10% w/v) was prepared in WFI;

b) Stock solution of. Protein of SEQ. ID NO. I was prepared in TBS (Tris buffer saline)) and was taken in a glass beaker;

c) required quantity of Polysorbate-80 solution from step a) was transferred in the glass beaker of step b) at a temperature of 22° C.-25° C. and mixed well to obtain clear colourless solution;

d) required quantity of L-Arginine hydrochloride (L-Arginine HCl) was added to the solution of step c) and was mixed well for homogenous dissolution;

e) required quantity of sucrose was added to the solution of step d) and mixed well for homogenous dissolution;

f) pH of the solution in step e) was adjusted between 7.4-8.0 (using 0.05N Hydrocloric acid);

g) Final batch size was arrived at using WFI;

h) Final batch was filtered through 0.22 micron PVDF filter followed by filling, stoppering and capping.

Example 2: Formulation of Recombinant Protein without any Stabilizer and Solubilizer

| Ingredients | mg/mL |
| --- | --- |
| SEQ ID NO. 1 | 5.0 |
| Tris | 3.03 |
| NaCl | 4.38 |
| Hydrochloric acid | Quantum satis (q.s.) to pH |
| Water for injection | q.s to 1 mL |

Procedure for Preparation:

a) stock solution of protein of SEQ ID NO. I in TBS (Tris buffer saline) was taken in a glass beaker;

b) pH of the solution was adjusted between 7.4-8.0 (using 0.05N MCI);

c) final batch size was made up using WFI;

d) batch was filtered through 0.22 micron PVDF filter followed by filling, stoppering and capping.

e) filled vials were stored at 2° C.-8° C. temperature.

Stability results: Significant drop in assay observed after 3 months storage at 2° C. 8° C.

Example 3: Formulation with L-Histidine

| Ingredients | mg/mL |
| --- | --- |
| SEQ ID NO. 1 | 7.5 |
| Tris | 4.4 |
| NaCl | 6.36 |
| Polysorbate 80 | 1 |
| 1 . . . -Histidine | 3.87 |
| Hydrochloric acid | q.s. to pH |
| Water for injection | q.s to I mi . . . , |

Above formulation was prepared by the process as in Example I.

Stability results: Visual inspection exhibited white precipitate after one month of preparation when stored at 25° C./60% RH. (Relative Humidity)

Example 4: Liquid Formulation of Recombinant Protein

| Ingredients | mg/mL |
| --- | --- |
| SEQ ID NO. 1 | 5 |
| Iris | 2.93 |
| NaCl | 4.24 |
| Polysorbate 80 | 1 |
| L-Arginine HCl | 5.27 |
| Sucrose | 10 |
| Hydrochloric acid | q.s. to pH |
| Water for injection | q.s to 1 ml. |

Above formulation was prepared by the process as in Example 1.

Stability Results: Stability results after three months of preparation when stored at 25° C./60% RH and 2° C.-8° C. were reported.

Visual inspection indicated clear and colourless solution after completion of three months, as was when prepared.

Assay results were reported to be within the acceptable limits (90%-110%) with no significant drop. The bioassay results were reported to be within the acceptable range of 31.58% and 58.05% for PA-1 cell lines.

Example 5: Liquid Formulation of Recombinant Protein

| Ingredients | mg/mL |
| --- | --- |
| SEQ ID NO. 1 | 7.5 |
| Tris | 4.4 |
| NaCl | 6.36 |
| Polysorbate 80 | I |
| L-Arginine MI | 5.$^1$7 |
| Sucrose | 10 |
| Hydrochloric acid | q.s. to pH |
| Water for injection | q.s to 1 mL, |

Above formulation was prepared by the process as stated in Example 1.

Stability Results: Visual inspection showed clear and colourless solution after three months at 25° C./60% RH and 2° C.-8° C.

Assay results were found within the limits (90%-110%) with no significant drop. The bioassay results were reported to be within the acceptable range of 31.58% and 58.05% for PA-1 cell lines.

Example 6: Liquid Formulation of Recombinant Protein

| Ingredients | mg/mL |
| --- | --- |
| SEQ ID NO. 1 | 7.5 |
| Tris | 4.4 |
| NaCl | 6.36 |

-continued

| Ingredients | mg/mL |
| --- | --- |
| Polysorbate 80 | 1 |
| L-Arginine MI | 3 |
| Sucrose | 10 |
| Hydrochloric acid | q.s. to pH |
| Water for injection | q.s to 1 mi, |

Above formulation was prepared by the process as in Example 1.

Stability Results: Stability results for six months at 25° C./60% RI-T and 2° C.-8° C. were reported. Visual inspection showed clear colourless solution over a period of 6 months.

Assay results were found to be within limits for 1 month, 2 months 3 months and 6 months with no considerable presence of high molecular weight impurities.

Bioassay results were within the limits of 31.58% and 58.05% for PA-1 cell lines.

Example 7: Lyophilized Formulation of Recombinant Protein

| Ingredients | mg/mL |
| --- | --- |
| SEQ ID NO. 1 | 1.25 |
| Tris | 0.73 |
| NaCl | 1.06 |
| Polysorbate 80 | 0.5 |
| L-Arginine HCl | 1 |
| Sucrose | 6 |
| Mannitol | 18 |

The above formulation was prepared by the following process:

a) stock solution of. Polysorbate 80 (10% w/v) was prepared in WFI;

b) stock solution of protein of SEQ ID NO. 1 was prepared in TBS (Tris buffer saline) and was taken into a glass beaker;

c) required quantity of Polysorbate-80 solution of step a) was added to the solution of step b) at a temperature of 22-25° C. and mixed well to obtain clear colourless solution appeared;

d) required quantity of 40% WFI was added to the solution of step c);

e) required quantity of L-Arginine HCl was added to the solution of step d) and was mixed well for homogenous dissolution;

f) required quantity of Sucrose was added to the solution of step e) and mixed well for homogenous dissolution;

g) mannitol was added to the solution of step 1) and mixed to get clear colourless solution;

h) pH of the solution in step g) was adjusted between 7.4-8.0 using 0.05N HCl;

i) WFT was added to solution in step h) to make up the batch size;

j) batch was filled in the vials and subjected for lyophilisation; k) lyophilized vials are stored at 2° C.-8° C. temperature.

Stability Results: Stability results for twelve months at 25° C./60% RH and 2° C.-8° C. were reported.

Visual inspection showed White lyophilized cake after 12 months indicating desired physical stability.

Assay results found to be within the limits and with no considerable variations. Bioassay results were within the limits of 31.58% and 58.05% for PA-1 cell lines.

Example 8: Lyophilized Formulation of Recombinant Protein

| Ingredients | Composition Before Lyophilisation (mg/mL) | Composition after reconstitution of lyophilized product (mg/mL) |
| --- | --- | --- |
| SEQ ID NO. 1 | 1.25 mg | 2.50 |
| Tris | 0.656 mg | 1.31 |
| NaCl | 0.950 mg | 1.90 |
| Polysorbate 80 | 0.50 mg | 1 |
| L-Arginine HCl | 1.00 mg | 2 |
| Sucrose | 12.00 mg | 24 |
| Mannitol | 36.00 mg | 72 |
| Hydrochloric acid | q.s. to pH | q.s. to pH |

The above formulation was prepared by the following process:

a) stock solution of Polysorbate 80 (10% w/v) was prepared in WFI. Required quantity of Polysorbate 80 was taken from this stock solution and added in the WFI.

b) stock solution of protein of SEQ ID NO. I. was prepared in TBS (Tris buffer saline) and was taken into a glass beaker;

c) required quantity of solution of protein of SEQ ID NO. 1 of step b) was added to the required quantity of solution of step a) at a temperature of 22° C.-25° C. and mixed well to obtain clear colourless solution appeared;

d) required quantity of L-Arginine HCl was added to the solution of step c) and was mixed well for homogenous dissolution;

e) required quantity of Sucrose was added to the solution of step d) and mixed well for homogenous dissolution;

f) required quantity of mannitol was added to the solution of step e) and mixed to get clear colourless solution;

g) the volume of the batch was made up to 80% of batch size using WFI.

h) pH of the solution in step g) was adjusted between 7.4-8.0 using 0.05N HCl;

i) WFI was added to solution in step h) to make up the batch size;

j) batch was filled in the vials and subjected for lyophilisation;

k) lyophilized vials were stored at 2° C.-8° C. temperature.

Stability Results: Stability results for six months at 25° C./60% RH and 2° C.-8° C. were reported.

Visual Inspection showed white cake free from visible particles over a period of six months. Assay results were found to be within the acceptable limits over period of one month, 2 months 3 months and 6 months respectively with no considerable presence of high molecular weight impurities. Bioassay results were within the limits of 31.58% and 58.05% for. PA-1 cell lines.

Reconstitution time was analysed by adding WFI in the vial containing lyophilized product.

Example 9: Formulation of Recombinant Protein
with L-Histidine

| ingredients | Mg/mL |
|---|---|
| SEQ ID NO. 1 | 7.5 |
| Tris | −1.4 |
| NaCl | 6.36 |
| Polysorbate 20 | 1 |

-continued

| ingredients | Mg/mL |
|---|---|
| L-Histidine | 3.87... |
| Sucrose | 10 . . . |
| Hydrochloric acid | q.s. to pH |
| Water for Injection | q.s to 1 ml. |

Above formulation was prepared by the process as stated in Example 1.

We claim:

1. A stable pharmaceutical composition comprising
   a therapeutically effective amount of a recombinant lectin protein derived from *Sclerotium rolfsii* lectin and comprising SEQ ID NO: 1 and
   pharmaceutically acceptable excipients;
   wherein the pharmaceutically acceptable excipients comprise
   a) arginine;
   and at least one of:
   b) Polysorbate 80 or sucrose,
      wherein the composition is characterized in that it maintains an at least 90% to 110% assay value and comprises less than 5% high molecular weight aggregates after storage for 3 months at 22-28° C., and
   wherein the stable pharmaceutical composition is capable of use for the treatment of cancer.

2. The stable pharmaceutical composition as claimed in claim 1, wherein the composition comprises the recombinant lectin protein in an amount from about 0.001 mg/ml to about 100 mg/ml.

3. The stable pharmaceutical composition as claimed in claim 1, wherein the arginine is present as a pharmaceutically acceptable salt selected from the group consisting of alkali salt, an alkaline earth metal salts, ammonium salts, organic amine salts, basic amino acid salts and acid salts.

4. The stable pharmaceutical composition as claimed in claim 1, wherein the concentration of the recombinant lectin protein is from about 0.001 mg/mL to about 100 mg/mL and the concentration of the arginine is from about 0.1 mg/mL to about 100 mg/mL.

5. The stable pharmaceutical composition as claimed in claim 1, wherein the ratio of recombinant lectin protein (mg/mL) to arginine (mg/mL) is from about 1:0.1 to about 1:10.

6. The stable pharmaceutical composition as claimed in claim 1, wherein the excipient comprises polysorbate 80, wherein the concentration of polysorbate 80 is from about 0.001 mg/ml to about 10 mg/ml.

7. The stable pharmaceutical composition as claimed in claim 1, wherein the excipient comprises polysorbate 80, wherein the ratio of recombinant lectin protein to polysorbate 80 is from about 1:0.0002 to about 1:10.

8. The stable pharmaceutical composition as claimed in claim 1, wherein the excipients comprise sucrose, wherein the sucrose has a concentration from about 1.0 mg/mL to about 150.0 mg/mL.

9. The stable pharmaceutical composition as claimed in claim 1, wherein the excipients comprise sucrose, wherein the ratio of arginine to sucrose is from about 1:0.1 to about 1:150.

10. The stable pharmaceutical composition as claimed in claim 1, wherein the composition is capable of being administered locally, enterally or parenterally.

11. The stable pharmaceutical composition as claimed in claim 1, wherein the excipients further comprise one or more excipients selected from buffers, polymers, solubilizers, cryoprotectants, lyoprotectants, bulking agents, diluents, emulsifiers or preservatives.

12. The stable composition claimed in claim 1, wherein the composition exhibits a cytotoxicity of 31.58% to 58.05% against an ovarian cancer PA-1 cell line during a stability period.

13. A process to prepare a stable pharmaceutical composition including a therapeutically effective amount of a recombinant lectin protein derived from *Sclerotium rolfsii* lectin and comprising SEQ ID NO: 1, and
    two or more pharmaceutically acceptable excipients;
    wherein the process comprises combining a buffer solution of the recombinant lectin protein with a buffer solution of said two or more pharmaceutically acceptable excipients, the pharmaceutically acceptable excipients being selected the such that the stable pharmaceutical composition maintains an assay value of 90% to 110% and less than 5% high molecular weight aggregates after storage for 3 months at 2-8° C.,
    wherein the two or more pharmaceutically acceptable excipients comprise
    a) arginine or its pharmaceutically acceptable salt; and
    at least one of
    b) polysorbate 80 or sucrose,
    wherein the stable pharmaceutical composition is capable of use for the treatment of cancer.

14. A stable pharmaceutical composition for the treatment of cancer, comprising about 0.0001% (w/v) to about 10% (w/v) of a recombinant lectin protein derived from *Sclerotium rolfsii* lectin and comprising SEQ ID NO: 1, wherein the pharmaceutical composition further comprises:
    a) about 0.01% (w/v) to about 10% (w/v) of arginine or its pharmaceutically acceptable salt; and
    at least one of
    b) about 0.0001% (w/v) to about 1% (w/v) of polysorbate 80; or
    c) about 0.1% (w/v) to about 15% (w/v) of sucrose.

* * * * *

SEQUENCE LISTING

```
<160> NUMBER OF SEQ ID NOS: 4

<210> SEQ ID NO 1
<211> LENGTH: 141
<212> TYPE: PRT
<213> ORGANISM: Artificial Sequence
<220> FEATURE:
<223> OTHER INFORMATION: Modified

<400> SEQUENCE: 1

Thr Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Thr Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                85                  90                  95

Ser Gln Lys Asn Arg Glu Glu Ala Arg Glu Arg Gln Leu Ser Asn Tyr
            100                 105                 110

Gln Val Lys Asn Ala Lys Gly Arg Asn Phe Gln Ile Val Tyr Thr Glu
        115                 120                 125

Ala Glu Gly Asn Asp Leu His Ala Asn Leu Ile Ile Gly
    130                 135                 140

<210> SEQ ID NO 2
<211> LENGTH: 141
<212> TYPE: PRT
<213> ORGANISM: Artificial Sequence
<220> FEATURE:
<223> OTHER INFORMATION: Modified

<400> SEQUENCE: 2

Val Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asn Gly Gly Thr
            20                  25                  30

Trp Ser Ile Thr Asp Asp Gln His Val Leu Thr Met Gly Gly Ser Gly
        35                  40                  45

Thr Ser Gly Thr Leu Arg Phe His Ala Asp Asn Gly Glu Ser Phe Thr
    50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
```

-continued

```
                    85                    90                    95

Ser Gln Lys Asn Arg Glu Glu Ala Arg Glu Arg Gln Leu Ser Asn Tyr
                    100                   105                   110

Gln Val Lys Asn Ala Lys Gly Arg Asn Phe Gln Ile Val Tyr Thr Glu
                115                   120                   125

Ala Glu Gly Asn Asp Leu His Ala Asn Leu Ile Ile Gly
        130                   135                   140

<210> SEQ ID NO 3
<211> LENGTH: 141
<212> TYPE: PRT
<213> ORGANISM: Artificial Sequence
<220> FEATURE:
<223> OTHER INFORMATION: Modified

<400> SEQUENCE: 3

Val Tyr Lys Ile Thr Val Arg Val Tyr Gln Thr Asn Pro Asp Ala Phe
1               5                   10                  15

Phe His Pro Val Glu Lys Thr Val Trp Lys Tyr Ala Asp Gly Gly Thr
                20                  25                  30

Trp Ser Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
        50                  55                  60

Ala Thr Phe Gly Val His Asp Tyr Lys Arg Trp Cys Asp Ile Val Thr
65                  70                  75                  80

Asp Leu Ala Ala Asp Glu Thr Gly Met Val Ile Asn Gln Glu Tyr Tyr
                    85                  90                  95

Ser Glu Lys Asp Arg Glu Glu Ala Arg Glu Arg Gln Asn Ser Asn Tyr
                    100                   105                   110

Glu Val Lys Asp Ala Lys Gly Arg Asn Phe Glu Ile Val Tyr Thr Glu
                115                   120                   125

Ala Glu Gly Asn Asp Leu His Ala Asp Leu Ile Ile Gly
        130                   135                   140

<210> SEQ ID NO 4
<211> LENGTH: 141
<212> TYPE: PRT
<213> ORGANISM: Artificial Sequence
<220> FEATURE:
<223> OTHER INFORMATION: Modified

<400> SEQUENCE: 4

Thr Tyr Lys Ile Thr Val Arg Val Tyr Gln Thr Asn Pro Asn Ala Phe
1               5                   10                  15

Phe His Pro Val Glu Lys Thr Val Trp Lys Tyr Ala Asn Gly Gly Thr
                20                  25                  30

Trp Thr Ile Thr Asp Asp Gln His Val Leu Thr Met Gly Gly Ser Gly
            35                  40                  45

Thr Ser Gly Thr Leu Arg Phe His Ala Asp Asn Gly Glu Ser Phe Thr
        50                  55                  60

Ala Thr Phe Gly Val His Asn Tyr Lys Arg Trp Cys Asp Ile Val Thr
65                  70                  75                  80

Asn Leu Ala Ala Asp Glu Thr Gly Met Val Ile Asn Gln Gln Tyr Tyr
                    85                  90                  95

Ser Gln Lys Asn Arg Glu Glu Ala Arg Glu Arg Gln Leu Ser Asn Tyr
                    100                   105                   110
```

-continued

```
Glu Val Lys Asn Ala Lys Gly Arg Asn Phe Glu Ile Val Tyr Thr Glu
        115                 120                 125

Ala Glu Gly Asn Asp Leu His Ala Asn Leu Ile Ile Gly
    130                 135                 140
```